United States Patent [19]

Schmolka

[11] Patent Number: 4,668,430
[45] Date of Patent: May 26, 1987

[54] ROLL-ON PERFUME COMPOSITIONS CONTAINING POLYOXYBUTYLENE-POLYOXYETHYLENE COPOLYMERS

[75] Inventor: Irving R. Schmolka, Grosse Ile, Mich.

[73] Assignee: BASF Corporation, Wyandotte, Mich.

[21] Appl. No.: 718,859

[22] Filed: Apr. 2, 1985

Related U.S. Application Data

[63] Continuation-in-part of Ser. No. 383,750, Jun. 1, 1982, abandoned.

[51] Int. Cl.$^4$ .............................. A61K 7/46; C11B 9/00
[52] U.S. Cl. ............................... 252/522 R; 252/522 A
[58] Field of Search ....................... 252/522 A, 522 R

[56] References Cited

U.S. PATENT DOCUMENTS

| 2,667,268 | 1/1954 | Griffin | 424/360 X |
| 3,579,465 | 7/1973 | Schmolka | 424/60 |
| 3,748,276 | 7/1973 | Schmolka | 424/60 |
| 4,089,814 | 5/1978 | Schmolka | 252/522 A |

OTHER PUBLICATIONS

Schick, Nonionic Surfactants, vol. 2, (1967) 326-337.

*Primary Examiner*—Bernard Helfin
*Attorney, Agent, or Firm*—William G. Conger

[57] ABSTRACT

The subject invention relates to roll-on perfume compositions containing polyoxybutylene-polyoxyethylene block copolymers having an internal polyoxybutylene hydrophobe and external polyoxyethylene hydrophiles.

19 Claims, No Drawings

ROLL-ON PERFUME COMPOSITIONS CONTAINING POLYOXYBUTYLENE-POLYOXYETHYLENE COPOLYMERS

This is a continuation-in-part application of co-pending U.S. application Ser. No. 383,750 filed June 1, 1982, now abandoned.

BACKGROUND OF THE INVENTION

1. Field of the Invention

The invention relates to roll-on perfume compositions containing a cogeneric mixture of polyoxybutylene-polyoxyethylene block copolymers. These copolymers, containing internal polyoxybutylene hydrophobes, possess exceptional viscosity increasing ability when compared to previously available thickeners.

2. Description of the Prior Art

It is known to use certain nonionic surfactants in liquid, roll-on perfume compositions to aid in spreading of the essential oil on the skin so as to obtain a uniform coating. The surfactant in such compositions must actually perform several functions. First it must aid in spreading the essential oil and other ingredients on the skin so as to obtain a uniform coating. Second, it must stabilize the composition with regard to preventing separation of its components. Finally, it must increase the viscosity to such a degree that leakage from the container is minimized.

Polyoxypropylene-polyoxyethylene copolymers have been used in such compositions. In U.S. Pat. No. 4,089,814, for example, roll-on perfume compositions are disclosed which comprise water, an essential oil, an alcohol or other solvent, and a polyoxyethylene-polyoxypropylene block copolymer represented by the formula:

$$HO(C_2H_4O)_b(C_3H_6O)_a(C_2H_4O)_bH$$

wherein a is an integer such that the hydrophobe represented by $(C_3H_6O)_a$ has a molecular weight of from 3250 to 4000 and b is an integer such that the hydrophile portion represented by $(C_2H_4O)_b$ constitutes from about 50 to 90 weight percent of the copolymer. The average total theoretical molecular weight of the copolymers of use range from 6550 to 40,000.

The roll-on perfume compositions of U.S. Pat. No. 4,089,814 contain a minimum of 20 parts by weight of the above polyoxyethylene-polyoxypropylene block copolymer. Due to the expensive nature of these pharma-grade surfactants, compositions which minimize the amount of surfactant required, while maintaining or increasing the viscosity of the composition are desirable.

SUMMARY OF THE INVENTION

It is therefore an object of the invention to develop liquid, roll-on perfume compositions in which a specified viscosity may be achieved with the use of lesser amounts of surfactant as compared to previous compositions. It is a further object of the invention to provide compositions which may have greatly increased viscosity without utilizing large amounts of surfactants and without gellation. These and other objects of the invention were met by the discovery that certain polyoxybutylene-polyoxyethylene block copolymer polyethers provide unexpectedly high viscosity increasing ability when utilized in roll-on perfume compositions. The use of these polyethers allows the formulator to prepare a composition of a given viscosity utilizing much less surfactant, or alternatively, to prepare essentially the same composition in a much more viscous version.

These and other objects of the invention were met by liquid, non-gelled roll-on perfume compositions comprising, based on 100 parts by weight of total composition, from 5 percent to 15 percent of a perfume oil, from 25 percent to 40 percent of a volatile alcohol, from 10 percent to 60 percent water, and from 10 percent to 30 percent of a nonionic polyether surfactant.

Preferably used as the copolymer are polyoxybutylene-polyoxyethylene block copolymers. These copolymers are a cogeneric mixture of polyoxybutylene-polyoxyethylene compounds containing in their structure internal oxybutylene groups, oxyethylene groups and an organic radical derived from an organic compound which contains a plurality of reactive hydrogen atoms and preferably from 2 to 6 or 8 carbon atoms. The copolymers are characterized in that all the oxybutylene groups are present in polyoxybutylene chains bonded to the organic radical at the site of a reactive hydrogen atom, thereby principally constituting a hydrophobic polyoxybutylene polymer. The hydrophobic polyoxybutylene chains terminate in polyoxyethylene hydrophiles. The average molecular weight of the polyoxybutylene hydrophobe in the mixture is at least 500, as determined by hydroxyl number, and the oxyethylene groups present constitute 50 to 90 percent, preferably 70 to 85 percent, and most preferably approximately 80 percent by weight of the compound. The polyoxybutylene-polyoxyethylene block copolymer polyethers must not form gels at the concentrations utilized.

The roll-on perfume compositions utilizing the polyoxybutylene-polyoxyethylene copolymer polyethers are clear, stable, viscous liquids. Their viscosity is unexpectedly higher than known products prepared from polyoxyethylene-polyoxypropylene copolymers and thus it is possible to use less polyoxybutylene-polyoxyethylene copolymer when formulating, or to achieve higher viscosities utilizing comparable amounts of surfactant.

DESCRIPTION OF THE PREFERRED EMBODIMENTS

The copolymer polyethers used in the invention are a cogeneric mixture of polyoxybutylene-polyoxyethylene block copolymers having an internal polyoxybutylene hydrophobe, and external polyoxyethylene hydrophiles comprising from 50 to 90 percent of the total polyether molecular weight. Thus the copolymer polyethers of the subject invention are nonionic polyether surfactants which are polyoxybutylene-polyoxyethylene block copolymers corresponding to the formula $$Y[(C_4H_8O)_n(C_2H_4O)_mH]_x \qquad (A)$$

wherein Y is an organic radical derived from an organic initiator molecule having x active hydrogens, and where the values of n and x are integers such that the internal polyoxybutylene hydrophobe, corresponding to that portion of the molecule represented by the formula $$Y[(C_4H_8O)_n]_x \qquad (B)$$

has a molecular weight of at least 500, and wherein the value of m in the external polyoxyethylene hydrophiles corresponding to those portions of the molecule represented by the formula $$[(C_2H_4O)_m]_x \quad (C)$$

is such that the hydrophiles comprise from 50 percent to about 90 percent by weight of the polyether.

The hydrophobic polyoxybutylene polymer, which is an intermediate in the preparation of the compounds of use in this invention, has the following structure:

$$Y[(C_4H_8O)_nH]_x \quad (D)$$

wherein Y, n and x are defined as in Formula A above. These polyoxybutylene polymers, which form the polyoxybutylene hydrophobe of the finished polyether, have molecular weights greater than 500, preferably greater than 2000, and most preferably between 3000 and 5000.

The preferred compounds of use in this invention are block copolymers prepared by condensing ethylene oxide with the polyoxybutylene polymer in an amount such that oxyethylene groups constitute between 50 and 90 percent preferably from 70 to 85 percent, and most preferably about 80 percent by weight of the resultant compound.

When ethylene oxide is condensed with a polyoxybutylene glycol of at least 500 molecular weight and derived from a butanediol initiator, the resulting compounds have the following structure:

$$HO(C_2H_4O)_m(C_4H_8O)_n(C_2H_4O)_mH \quad (E)$$

where n is defined as previously set forth; and m has a value such that the oxyethylene groups constitute 50 percent by weight to 90 percent by weight of the compound, preferably from 70 to 85 percent by weight, and most preferably approximately 80 percent by weight.

The hydrophilic portion of the polyoxyalkylene compounds may be supplied in whole or in part by other polyoxyalkylene chains in lieu of the polyoxyethylene chain set forth in Formula C. For example heteric polyoxyalkylene copolymer chains consisting predominately of oxyethylene residues with lesser quantities of oxypropylene or oxybutylene residues may be used.

In other words, the preferred cogeneric polyoxybutylene-polyoxyethylene block copolymers correspond to the formula $$HO(C_2H_4O)_m(C_4H_8O)_n(C_2H_4O)_mH$$

wherein m is an integer such that the molecular weight of the polyoxybutylene hydrophobe which is that portion of the molecule represented by the formula $$(C_4H_8O)_n$$

is greater than 500, and wherein n is an integer such that the polyoxyethylene hydrophiles which are those portions of the molecule represented by $$(C_2H_4O)_m$$

comprise from 50 percent to 90 percent by weight of the polyether.

Examples of organic initiator compounds containing x active hydrogen atoms are diols such as propanediol and butanediol, triols such as glycerol and trimethylolpropane, tetrols such as pentaerythritol, as well as initiators containing more than four hydroxyl groups such as hexitol or sucrose. Water may also be used as an initiator. Also, amines and other low molecular weight compounds having two or more active hydrogen atoms, such as ethylene diamine or diethylene triamine, may be used as the initiator. Preferably used are diols such as ethylene glycol, propylene glycol, and the butylene glycols. Most preferably, butylene glycol, 1,4-butanediol, is used as the initiator.

In making the hydrophobic polyoxybutylene polymer, which is an intermediate in the preparation of the compounds used in this invention, 1,2-butylene oxide is preferably used. However, other 4-carbon cyclic ethers may be used such as methyloxetane, tetrahydrofuran, and isobutylene oxide. The butylene oxide may be replaced with up to 10 percent by weight of propylene oxide or ethylene oxide when added as a mixture with the butylene oxide.

In preparing the hydrophilic portion of the copolymer, up to 10 percent by weight of propylene oxide or 1,2-butylene oxide may be used to replace ethylene oxide, and is added as a mixture with the ethylene oxide.

The preferred block copolymers of the invention conform to structure (E) set forth previously and have a hydrophobe molecular weight of at least 2400, preferably 3000 to 5000, and an ethylene oxide content of from about 50 percent by weight to about 90 percent by weight, preferably 70 percent by weight to 85 percent by weight of the block copolymer. The block copolymer is used in an amount between 10 percent by weight and 30 percent by weight of the roll-on perfume composition.

Useful as essential oils are ingredients which provide the scent to the perfume compositions. There are numerous essential oils, sometimes known simply as perfumes, both natural and synthetic, which may be employed in the invention. Almost all essential oils are mixtures of various ingredients. Reference is made to the two-volume treatise *Perfumes, Cosmetics, and Soaps,* 1936, D. Van Nostrand Company, Inc., and "Isolates for Perfumery," Second Edition, 1961, Givaudan-Delawanna, Inc. for a description of various essential oils. All the essential oils there described may be employed in the subject invention. The particular essential oil employed in the formulation of the compositions of the subject invention is not critical to the invention.

Another ingredient of the compositions of the subject invention is an alcohol, preferably lower alkanols such as ethanol, propanol, isopropanol, t-butanol, sec-butanol and n-butanol. Other alcohols which may be employed include propylene glycol, sorbitol, glycerol, dipropylene glycol, pentaerythritol and trimethylolpropane.

The roll-on perfume compositions of the subject invention are prepared by adding the copolymer to a water-alcohol solution at a temperature of about 75° C. and thereafter adding the essential oil and any other ingredients thereto.

In the examples which follow, block copolymers A, B, and C were used to prepare the roll-on perfume compositions. These were prepared by condensing ethylene oxide with a polyoxybutylene hydrophobe prepared by condensing 1,2-butylene oxide with 1,4-butanediol as an initiator.

Copolymer A is a polyoxybutylene-polyoxyethylene block copolymer having an approximate average molecular weight of the polyoxybutylene hydrophobe of 3000 and a polyoxyethylene hydrophile content of about 80 percent by weight of the block copolymer. The total molecular weight of the copolymer is about 15,000.

Block copolymer B is a polyoxybutylene-polyoxyethylene block copolymer having an approximate average molecular weight of the polyoxybutylene hydrophobe of 3000 and a polyoxyethylene hydrophile content of about 60 percent by weight of the block copolymer. The total molecular weight of the copolymer is about 7500.

Block copolymer C is polyoxybutylene-polyoxyethylene block copolymer having an approximate average molecular weight of the polyoxybutylene hydrophobe of 2400 and a polyoxyethylene hydrophile content of about 80 percent by weight of a block copolymer. The total molecular weight of the copolymer is about 12,000.

Block copolymer M, for comparison purposes, is a polyoxyethylene-polyoxypropylene block copolymer having an internal polyoxypropylene hydrophobe with a nominal molecular weight of about 4000 and external polyoxyethylene hydrophiles which comprises of about 70 percent of the total weight of the block copolymer. The total molecular weight of the copolymer is about 13,500.

Block copolymer N, for comparison purposes, is a polyoxyethylene-polyoxypropylene block copolymer having an internal polyoxypropylene hydrophobe with a nominal molecular weight at 2750 and external polyoxyethylene hydrophiles which comprise 80 percent of the total weight of the block copolymer. The total molecular weight of the copolymer is approximately 13,700.

Essential oils A–E used in the examples are as follows:

A is M2339, Stepan - Chardrene
B is E585927, Givaudan - Rose Floral Bouquet
C is M2430, Stepan - French Floral Bouquet
D is VF-2118-1, Givaudan - Spicy Powder Jasmine Chypre
E is 510542, Secret Underarm Floral The following examples will further illustrate the various aspects of the invention. Where not otherwise specified throughout this specification and claims, temperatures are in degrees centigrade, and parts, percentages and proportion are by weight.

EXAMPLES 1–5

In Examples 1–5, clear thickened roll-on perfume compositions of the invention were prepared according to the preceding description of preparation. The ingredients used and the resulting viscosities in centistokes (CTS) are presented in Table I:

TABLE I

| Component | 1 | 2 | 3 | 4 | 5 |
|---|---|---|---|---|---|
| | | (percent by weight) | | | |
| Block Copolymer A | 17.1 | 23.0 | 26 | 14.9 | 21 |
| 95% ethanol | 36.6 | 32.7 | 33 | 40.4 | 33 |
| Water | 37.4 | 36.3 | 31 | 36.9 | 36 |
| Perfume Oil | | | | | |
| A | | 8.9 | | | |
| B | | | 8.0 | | |
| C | | | | 10 | |
| D | | | | 7.8 | |
| E | | | | | 10 |
| Viscosity (CTS) | 667 | 750 | 782 | 387 | 1092 |

Examples 1–5 were then duplicated except that copolymers M and N were used for comparison purposes. The viscosities of the resulting products are shown in Table II which follows. A comparison Table I and II shows that the viscosities of the composition of the subject invention are much higher than the viscosities of the corresponding compositions of the Comparison Examples.

This unexpectedly higher viscosity enables the formulator to use less of the polyoxybutylene-polyoxyethylene copolymer. Moreover, more water and less alcohol can be used which minimizes the drying of the skin.

TABLE II

| Comparison Example | (comparison) Block Copolymer | Viscosity CTS |
|---|---|---|
| C1 | M | 229 |
| C2 | M | 107 |
| C3 | M | 92 |
| C4 | M | 71 |
| C5 | M | 273 |
| C6 | N | 106 |

Table III is a summary showing side-by-side viscosities of the examples of the subject invention (1–5) and the prior art (C1–C6). The dramatic increase in viscosity for otherwise similar compositions is readily seen.

TABLE III

| Subject Invention Example | Viscosity (Centistokes) | Comparative (Prior Art) | Viscosity (Centistokes) |
|---|---|---|---|
| 1 | 667 | C1 | 229 |
| 2 | 750 | C2 | 107 |
| 3 | 782 | C3 | 92 |
| 3 | 782 | C6 | 106 |
| 4 | 387 | C4 | 71 |
| 5 | 1092 | C5 | 273 |

Table IV more completely summarizes the comparison between Example 3 of the subject invention and two analogous prior art compositions, C3 and C6.

TABLE IV

| | Example 3 (Subject Invention) | Comparison Example C6 (Schmolka '814) | Comparison Example C3 (Schmolka '814) |
|---|---|---|---|
| 95% Ethanol | 33.0 | 33.0 | 33.0 |
| Water | 31.0 | 31.0 | 31.0 |
| Fragrance Oil | 10.0 | 10.0 | 10.0 |
| Polyether Amount | 26.0 | 26.0 | 26.0 |
| Polyether Type | | | |
| (a) hydrophobe | 3000 m.w. polyoxybutylene | 2750 m.w. polyoxypropylene | 4000 m.w. polyoxypropylene |
| (b) hydrophile* | 80% polyoxyethylene | 80% polyoxyethylene | 70% polyoxyethylene |
| Viscosity (CTS) | 782 | 106.4 | 92 |

*percent total molecular weight due to hydrophile weight.

EXAMPLES 6 AND 7

Examples 6 and 7 were prepared using the procedure described for Examples 1–5. The compositions are shown as follows:

EXAMPLE 6

| Ingredients | Percent by Weight |
| --- | --- |
| Copolymer B | 21 |
| 95 percent ethanol | 33 |
| Water | 36 |
| Perfume Oil E | 10 |

EXAMPLE 7

| Ingredients | Percent by Weight |
| --- | --- |
| Copolymer C | 21 |
| Ethanol | 33 |
| Water | 36 |
| Perfume Oil E | 10 |

The embodiments of the invention in which an exclusive privilege or property is claimed are defined as follows:

1. In a liquid roll-on composition containing, in weight percent based upon the total composition weight, from 5 percent to 15 percent of a perfume oil, from 25 percent to 40 percent of a volatile alcohol, from 10 percent to 60 percent water, and from 10 percent to 30 percent of a nonionic polyether surfactant, the improvement comprising, employing as the nonionic polyether surfactant a cogeneric polyoxybutylene-polyoxyethylene block copolymer corresponding to the formula $$Y[(C_4H_8O)_n(C_2H_4O)_mH]_x$$

where Y is an organic radical derived from an organic initiator molecule having x active hydrogens, and where the values of n and x are integers such that an internal polyoxybutylene hydrophobe, corresponding to that portion of the molecule represented by the formula $$Y[(C_4H_8O)_n]_x$$

has a molecular weight of at least 500, and wherein the value of m in the external polyoxyethylene hydrophiles corresponding to those portions of the molecule represented by the formula $$[(C_2H_4O)_m]_x$$

is such that the hydrophiles comprise from 50 percent to about 90 percent by weight of the polyether.

2. The composition of claim 1 wherein said polyether contains polyoxyethylene hydrophiles which comprise from about 70 percent to 85 percent by weight of the polyether.

3. The composition of claim 1 wherein said internal polyoxybutylene hydrophobe has a molecular weight greater than 2000.

4. The composition of claim 1 wherein said polyoxybutylene hydrophobe has a molecular weight of from 3000 to 5000.

5. The composition of claim 1 wherein said volatile alcohol is selected from the group consisting of ethanol, propanol, isopropanol, t-butanol, sec-butanol, and n-butanol.

6. The composition of claim 2 wherein said volatile alcohol is selected from the group consisting of ethanol, propanol, isopropanol, t-butanol, sec-butanol, and n-butanol.

7. The composition of claim 3 wherein said volatile alcohol is selected from the group consisting of ethanol, propanol, isopropanol, t-butanol, sec-butanol, and n-butanol.

8. The composition of claim 4 wherein said volatile alcohol is selected from the group consisting of ethanol, propanol, isopropanol, t-butanol, sec-butanol, and n-butanol.

9. The composition of claim 1 wherein said organic initiator molecule is selected from the group consisting of ethylene glycol, propylene glycol, 1,2-butylene glycol, 1,3-butylene glycol, and 1,4-butylene glycol.

10. The composition of claim 3 wherein said organic initiator molecule is selected from the group consisting of ethylene glycol, propylene glycol, 1,2-butylene glycol, 1,3-butylene glycol, and 1,4-butylene glycol.

11. The composition of claim 5 wherein said organic initiator molecule is selected from the group consisting of ethylene glycol, propylene glycol, 1,2-butylene glycol, 1,3-butylene glycol, and 1,4-butylene glycol.

12. The composition of claim 9 wherein said organic initiator molecule is 1,4-butylene glycol.

13. In a liquid roll-on composition containing, in weight percent based upon the total composition weight, from 5 percent to 15 percent of a perfume oil, from 25 percent to 40 percent of a volatile alcohol, from 10 percent to 60 percent water, and from 10 percent to 30 percent of a nonionic polyether surfactant, the improvement comprising, employing as the nonionic polyether surfactant a cogeneric polyoxybutylene-polyoxyethylene block copolymer corresponding to the formula $$HO(C_2H_O)_m(C_4H_8O)_n(C_2H_4O)_mH$$

wherein m is an integer such that the molecular weight of the polyoxybutylene hydrophobe which is that portion of the molecule represented by the formula $$(C_4H_8O)_n$$

is greater than 500, and wherein m is an integer such that the polyoxyethylene hydrophiles which are those portions of the molecule represented by $$(C_2H_4O)_m$$

comprise from 50 percent to 90 percent by weight of the polyether.

14. The composition of claim 13 wherein said polyoxybutylene hydrophobe is prepared by oxyalkylating an organic initiator molecule which is 1,4-butylene glycol with a cyclic ether selected from the group consisting of 1,2-butylene oxide and tetrahydrofuran.

15. The composition of claim 13 wherein said polyoxybutylene hydrophobe has a molecular weight of greater than 2400.

16. The composition of claim 13 wherein said polyoxybutylene hydrophobe has a molecular weight of from 3000 to 5000.

17. The composition of claim 16 wherein said oxyethylene hydrophiles comprise from 70 to 85 percent by weight of the polyether.

18. The composition of claim 16 wherein said oxyethylene hydrophiles comprise about 80 percent by weight of the polyether.

19. The composition of claim 18 wherein said volatile alcohol is ethanol.

* * * * *